United States Patent [19]

Goldmann et al.

[11] Patent Number: 4,492,703
[45] Date of Patent: Jan. 8, 1985

[54] 4-(2-SUBSTITUTED PHENYL)-1,4-DIHYDROPYRIDINE-3,5-DICARBOXYLIC ACID ESTERS ACTIVE ON BLOOD CIRCULATION

[75] Inventors: Siegfried Goldmann, Wuppertal; Horst Böshagen; Jürgen Stoltefuss, both of Haan; Matthias Schramm, Cologne; Günter Thomas; Stanislav Kazda, both of Wuppertal, all of Fed. Rep. of Germany

[73] Assignee: Bayer Aktiengesellschaft, Leverkusen, Fed. Rep. of Germany

[21] Appl. No.: 468,819

[22] Filed: Feb. 22, 1983

[30] Foreign Application Priority Data

Mar. 5, 1982 [DE] Fed. Rep. of Germany ....... 3207982

[51] Int. Cl.$^3$ ................ A61K 31/455; C07D 211/82
[52] U.S. Cl. ..................................... 424/266; 546/321
[58] Field of Search ............... 546/139, 141, 142, 143, 546/144, 146, 147, 153, 156, 159, 162, 176, 255, 256, 257, 258, 271, 273, 275, 278, 279, 280, 281, 283, 284, 321; 544/238, 284, 297, 298, 300, 333, 353, 354, 355, 356, 405; 424/250, 251, 258, 266

[56] References Cited

U.S. PATENT DOCUMENTS

| | | | |
|---|---|---|---|
| 3,883,543 | 5/1975 | Bossert | 260/295.5 B |
| 3,923,818 | 12/1975 | Bossert | 260/294.8 G |
| 3,959,296 | 5/1976 | Bossert | 260/294.8 G |
| 3,968,117 | 7/1976 | Bossert | 260/295.5 R |
| 3,971,796 | 7/1976 | Bossert | 260/294.8 F |
| 4,096,270 | 6/1978 | Teulon | 424/266 |
| 4,188,395 | 2/1980 | Bossert | 424/266 |
| 4,219,653 | 8/1980 | Kastron | 546/322 |

FOREIGN PATENT DOCUMENTS

2509727 1/1983 France .

OTHER PUBLICATIONS

CA Bossert, F. et al., "Coronary Dilating 1,4-Dihydropyridine-3,5-Dicarboxylates," In *Chem. Abstracts* 80: 14958g, (1973).
Dzhemilev, U. M. et al., "New Method for the Dehydrogenation of 1,4-Dihydropyridines," In *Chemical Abstracts* 89: 43046z, (1978).
Kawai, R. et al., "4-Substituted 1,4-Dihydropyridine Derivatives," In *Chemical Abstracts* 79: 31902f, (1973).
Vincent, M., et al., "Diethyl 1,4-Dihydro-4-Phenyl-3,-5-Pyridinedicarboxylates," In *Chemical Abstracts* 81: 169440b, (1974).
Rodenkirchen, R. et al., "Structure-Activity Studies on Nifedipine in Isolated Cardiac Muscle," In *Chemical Abstracts* 92: 140421n, (1979).
Wehinger, E. et .al., "Dihydropyridines With Substituted Ester Groups," In *Chemical Abstracts* 93: 168138v, (1978).

*Primary Examiner*—Henry R. Jiles
*Assistant Examiner*—Dale A. Bjorkman
*Attorney, Agent, or Firm*—Sprung, Horn, Kramer & Woods

[57] ABSTRACT

1,4-Dihydropyridines of the formula

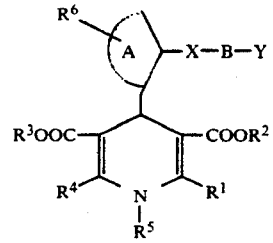

in which
$R^1$, $R^4$, $R^5$, $R^6$ and Y are hydrogen or various organic radicals,
$R^2$ and $R^3$ are various organic radicals,

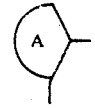

is phenyl, naphthyl or various heterocyclic radicals,
X is a direct bond, O, S or SO, and
B is a direct bond or alkylene, or pharmaceutically acceptable addition salts thereof exhibit hypotensive, vasodilating and coronary activities.

13 Claims, No Drawings

4-(2-SUBSTITUTED PHENYL)-1,4-DIHYDROPYRIDINE-3,5-DICARBOXYLIC ACID ESTERS ACTIVE ON BLOOD CIRCULATION

The present invention relates to new 1,4-dihydropyridines, several processes for their preparation and their use in medicaments, in particular in medicaments acting on the circulation.

It has already been disclosed that diethyl 1,4-dihydro-2,6-dimethyl-4-phenylpyridine-3,5-dicarboxylate is obtained when ethyl benzylideneacetoacetate is reacted with ethyl $\beta$-aminocrotonate or ethyl acetoacetate and ammonia (E. Knoevenagel, Ber. dtsch. chem. Ges. 31, 743 (1898)).

It has also been disclosed that certain 1,4-dihydropyridines have interesting pharmacological properties (F. Bossert, W. Vater, Naturwissenschaften 58, 578 (1971), DOS (German Published Specification) No. 2,117,571).

The present invention relates to new 1,4-dihydropyridines of the general formula I

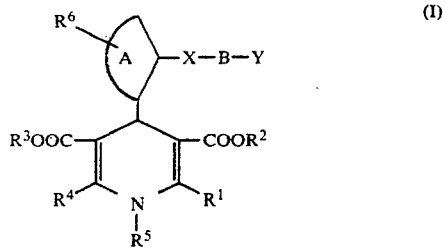

in which $R^1$ and $R^4$ are identical or different and each represent hydrogen or a straight-chain, branched or cyclic saturated or unsaturated aliphatic hydrocarbon radical, which optionally contains one or two identical or different hetero chain members from the group comprising O, CO, NH, N-alkyl, S or $SO_2$ and which is optionally substituted by halogen, nitro, cyano, azido, hydroxyl, aryl, aralkyl, heteroaryl, amino, monoalkylamino or dialkylamino, $R^2$ and $R^3$ are identical or different and each represent a straight-chain, branched or cyclic saturated or unsaturated aliphatic hydrocarbon radical, which is optionally substituted by halogen, hydroxyl, cyano, alkoxy, alkylthio, aryloxy, alkoxycarbonyl, amino, monoalkylamino, dialkylamino, alkylaralkylamino, aralkylamino or by a 5- to 7-membered heterocyclic ring, $R^5$ represents hydrogen, aryl, aralkyl or a straight-chain or branched alkyl radical, which is optionally substituted by alkoxy or halogen,

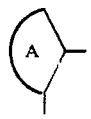

represents phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, $R^6$ represents one or two identical or different substituents from the group comprising hydrogen, alkyl, alkenyl, alkinyl, alkoxy, alkenoxy, alkinoxy, phenyl, alkylene, dioxyalkylene, halogen, trifluoromethyl, nitro, cyano, azido, carboxyl, hydroxyl, amino, alkylamino, halogenoalkoxy, carboalkoxy, carboxamido, sulphonamido, or $SO_m$.alkyl (m=0, 1 or 2), X represents a bridging member from the group comprising O, S, SO or a direct bond, B represents a straight-chain or branched alkylene group or a single bond (excepting X—B—Y=—O—O—), Y represents hydrogen, aryl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, cycloalkyl or alkenyl having at least 6 C atoms, these radicals either being directly bonded to B or bonded to B via a hetero atom from the group comprising O, S, SO, $SO_2$, NH or N-alkyl, and these radicals optionally containing 1, 2 or 3 identical or different substituents from the group comprising nitro, cyano, halogen, trifluoromethyl, hydroxyl, azido, carboxyl, phenyl, alkyl, alkenyl, alkoxy, alkenoxy, alkylene, dioxyalkylene, halogenoalkoxy, alkylamino, carboalkoxy, carboxamido, sulphonamido, alkylmercapto or $SO_2$-alkyl, and their pharmaceutically acceptable addition salts.

The compounds of the general formula (I) according to the invention can be prepared by (A) reacting ylidene-$\beta$-ketoesters of the general formula (II)

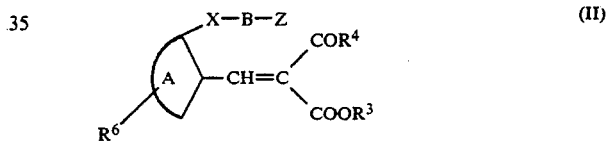

in which

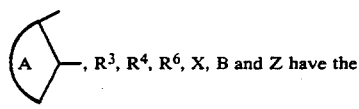, $R^3$, $R^4$, $R^6$, X, B and Z have the abovementioned meaning, with enaminocarboxylates of the general formula (III)

$$R^1-C=CH-COOR^2 \atop R^5NH \qquad (III)$$

in which $R^1$, $R^2$ and $R^5$ have the abovementioned meaning, if appropriate, in the presence of inert organic solvents at temperatures between 20° and 150° C., or (B) reacting ylidene-$\beta$-ketoesters of the general formula (II)

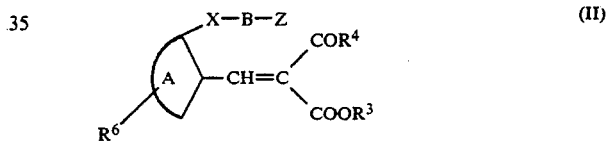

in which

, $R^3$, $R^4$, $R^6$, X, B and Z have the above-mentioned meaning, with amines of the general formula (IV)

$$R^5-NH_2 \qquad (IV)$$

in which $R^5$ has the abovementioned meaning, and β-ketocarboxylates of the general formula (V)

$$R^1-CO-CH_2-COOR^2 \qquad (V)$$

in which $R^1$ and $R^2$ have the abovementioned meaning, if appropriate, in the presence of inert organic solvents at temperatures between 20° and 150° C., or (C) reacting aldehydes of the general formula (VI)

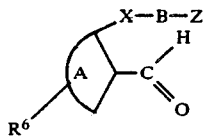 (VI)

in which

, $R^6$, X, B and Z have the abovementioned meaning, with enaminocarboxylates of the general formula (III)

$$R^1-C=CH-COOR^2 \qquad (III)$$
$$\quad |$$
$$R^5NH$$

in which $R^1$, $R^2$ and $R^5$ have the abovementioned meaning, and β-ketocarboxylates of the general formula (VII)

$$R^4-CO-CH_2-COOR^3 \qquad (VII)$$

in which $R^3$ and $R^4$ have the abovementioned meaning, if appropriate, in the presence of inert organic solvents at temperatures between 20° and 150° C., or (D) reacting aldehydes of the general formula (VI)

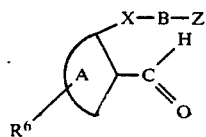 (VI)

in which

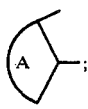;

$R^6$, X, B and Z have the abovementioned meaning, with amines of the general formula (IV)

$$R^5-NH_2 \qquad (IV)$$

in which $R^5$ has the abovementioned meaning, and two equivalents of β-ketoesters of the general formula (VII)

$$R^4-CO-CH_2-COOR^3 \qquad (VII)$$

in which $R^3$ and $R^4$ have the abovementioned meaning, if appropriate, in the presence of inert organic solvents at temperatures between 20° and 150° C.

The new dihydropyridines of the general formula (I) according to the invention have valuable pharmaceutical properties. Due to their activity on circulation, they can find use as antihypertensive agents, as vasodilators, as cerebral therapeutic agents and as coronary therapeutic agents.

Of particular interest are compounds of the general formula (I), in which $R^1$ and $R^4$ are identical or different and each represent hydrogen or a branched, unbranched or cyclic saturated or unsaturated aliphatic hydrocarbon radical having up to 6 carbon atoms, which is optionally substituted by halogen, hydroxyl, cyano, amino, phenyloxy, alkoxy, alkylthio, monoalkylamino, dialkylamino or alkoxycarbonyl, the alkyl and alkoxy radicals mentioned each containing 1 to 4 carbon atoms, $R^2$ and $R_3$ are identical or different and each represent a branched, unbranched or cyclic saturated or unsaturated aliphatic hydrocarbon radical having up to 10 carbon atoms, which is optionally substituted by halogen, hydroxyl, cyano, amino, phenyl, phenyloxy, alkoxy, alkylthio, monoalkylamino, dialkylamino or alkylbenzylamino, $R^5$ represents hydrogen, aryl or aralkyl, the aryl radicals containing 6 or 10 carbon atoms and the alkyl radical 1 to 4 carbon atoms, or $R^5$ represents a straight-chain or branched alkyl radical having up to 6 carbon atoms, which is optionally interrupted by 1 or 2 oxygen atoms in the alkyl chain or is substituted by halogen,

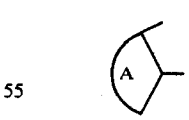

represents phenyl, naphthyl, thienyl, furyl, pyridyl, quinolyl or isoquinolyl, $R^6$ represents one or two identical or different substituents from the group comprising hydrogen, alkyl having 1 to 4 carbon atoms, alkenyl having up to 4 carbon atoms, alkoxy having up to 4 carbon atoms, phenyl, alkylene and dioxyalkylene, each having up to 4 carbon atoms, halogen, trifluoromethyl, nitro, cyano, azido, carboxyl, hydroxyl, amino, alkylamino having up to 6 C atoms in the alkyl group in each case, halogenoalkoxy having up to 4 carbon atoms, carboxyamido, carboalkoxy having 1 to 4 carbon atoms in the alkoxy radical, sulphonamido or $SO_m$-alkyl (m=0 or 2), X represents a bridging member from the group comprising O, S or SO or a single bond, B represents a straight-chain or branched alkylene group having up to 6 carbon atoms, and Y represents hydrogen, aryl having 6 to 10 carbon atoms, thienyl, furyl, pyrryl, pyrazolyl, imidazolyl, oxazolyl, thiazolyl, pyridyl, pyrimidyl, quinolyl, isoquinolyl, indolyl, benzimidazolyl, cycloalkyl having 3 to 7 carbon atoms or alkenyl having 6 to 12 carbon atoms, these radicals either being directly bonded to B or bonded to B via a hetero atom from the group comprising O, S, SO, $SO_2$, NH or N-alkyl, and these radicals optionally containing 1, 2 or 3 identical or different substituents from the group comprising nitro, cyano, halogen, trifluoromethyl, hydroxyl, azido, carboxyl, phenyl, alkyl having 1 to 4 carbon atoms, alkenyl having up to 4 carbon atoms, alkoxy having 1 to 4 carbon atoms, alkylene having 2 to 4 carbon atoms, dioxyalkylene having 2 or 3 carbon atoms, halogenoalkoxy having 1 to 4 carbon atoms, alkylamido having 1 to 4 carbon atoms in the alkyl radicals in each case, alkylmercapto or $SO_2$-alkyl each having 1 to 4 carbon atoms in the alkyl radicals.

Particular attention may be drawn to compounds of the general formula (I) in which $R^1$ and $R^4$ are identical or different and represent hydrogen or a straight-chain or branched alkyl radical which optionally contains 1 or 2 identical or different hetero chain members from the group comprising O, CO, NH or N-alkyl having 1 to 4 carbon atoms, and which is optionally substituted by halogen, nitro, cyano, hydroxyl, amino or phenyl, $R^2$ and $R^3$ are identical or different and each represent a branched or unbranched alkyl or alkenyl radical having up to 6 carbon atoms, which is optionally substituted by halogen, hydroxyl, cyano, amido, monoalkylamino, dialkylamino or alkylbenzylamino, the alkyl radicals mentioned each containing 1 to 4 carbon atoms, $R^5$ represents hydrogen, benzyl or a straight-chain or branched alkyl radical having up to 6 carbon atoms, which is optionally substituted by fluorine, chlorine or alkoxy having 1 to 4 carbon atoms,

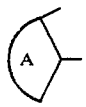

represents phenyl, naphthyl, thienyl, furyl or pyridyl, $R^6$ represents one or 2 identical or different substituents from the group comprising hydrogen, alkyl, alkoxy, each having 1 to 4 carbon atoms, fluorine, chlorine, bromine, cyano, trifluoromethyl, carboxyl, amino, hydroxyl, alkylamino or halogenoalkoxy, each having 1 to 4 carbon atoms, X represents a bridging member from the group comprising O, S or SO, B represents a straight-chain or branched alkylene group having 1 to 4 carbon atoms and Y represents phenyl, phridyl, cycloalkyl having 3 to 7 carbon atoms or alkenyl having 6 to 10 carbon atoms, these radicals being either directly bonded to A or bonded to B via a hetero atom from the group comprising O, S, SO, $SO_2$, NH or N-alkyl having 1 to 4 carbon atoms, and these radicals optionally containing 1 or 2 identical or different substituents from the group comprising nitro, halogen, trifluoromethyl, cyano, hydroxyl, phenyl, alkyl and alkoxy, each having 1 to 4 carbon atoms, and their pharmaceutically acceptable addition salts.

From a knowledge of the state of the art, it could not be predicted that substances, which are distinguished by advantageous biological properties, would be obtained by introducing the new substituents in the 4-position of the dihydropyridines. Due to their unexpected pharmaceutical activity, they represent an enrichment of the art.

Depending on the type of starting materials employed, the synthesis of the compounds of the general formula (I) according to the invention by the individual variants of the process can be represented by the reaction scheme below:

PROCESS VARIANT A

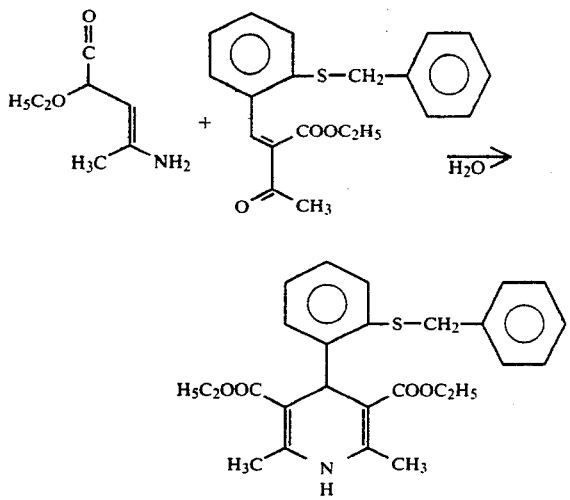

PROCESS VARIANT B

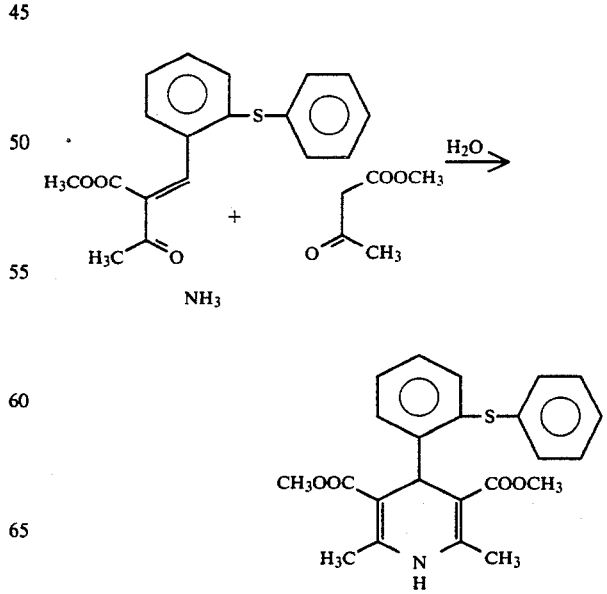

PROCESS VARIANT C

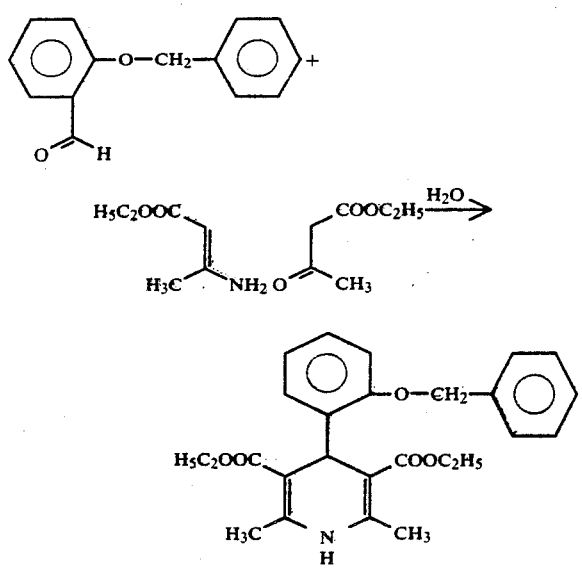

PROCESS VARIANT D

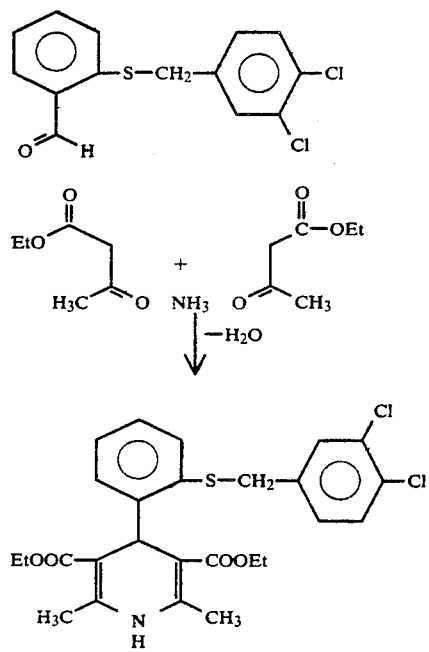

The ylidene-β-ketoesters of the formula (II) used as starting materials can be prepared by methods known from the literature (compare G. Jones, "The Knoevenagel Condensation", in Org. Reactions, Vol. XV, 204 et seq. (1967)).

Enaminocarboxylates (III) used as starting materials are known and can be prepared by methods known from the literature (compare A. C. Cope, J. Am. Chem. Soc. 67, 1,107 (1945)).

β-Ketocarboxylates (V) used as starting materials are known and can be prepared by methods known from the literature (for example D. Borrmann, "Umsetzung von Diketen mit Alkoholen, Phenolen and Mercaptanen" ("Reaction of Diketene with Alcohols, Phenols and Mercaptans") in Houben-Weyl, Methoden der organischen Chemie (Methods of Organic Chemistry) Vol. VII/4, 230 et seq. (1968); Y. Oikawa, K. Sugano and O. Yonemitsu, J. Org. Chem. 43, 2,087 (1978)).

Aldehydes (VI) used as starting materials are known and can be prepared by methods known from the literature (compare T. D. Harris and G. P. Roth, J. org. Chem. 44, 146 (1979), German Offenlegungsschrift (German Published Specification) No. 2,165,260, July 1972, German Offenlegungsschrift (German Published Specification) No. 2,401,665, July 1974, Mijano et al, Chem. Abst. 59 (1963), 13 929 c, E. Adler and H. -D. Becker, Chem. Scand. 15, 849 (1961), E. P. Papadopoulos, M. Mardin and Ch. Issidoridis, J. Org. Chem. 31, 615 (1966), J. Am. chem. Soc. 78, 2,543 (1956)).

For all the process variants A, B, C and D, all inert organic solvents are suitable as diluents. These include, preferably, alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a relatively large range. In general, the process is carried out between 20° and 150° C., but preferably at the boiling point of the particular solvent.

The reaction can be carried out under normal pressure or under elevated pressure. In general, the process is carried out under normal pressure.

The processes for preparation above are only mentioned for elucidation, and the preparation of the compounds of the formula (I) is not restricted to these processes, but any modification of these processes can be used in the same manner for the preparation of the compounds according to the invention.

Depending on the choice of the starting substances, the compounds according to the invention can exist in stereoisomeric forms which are related to one another either as image and mirror image (enantiomers) or which are not related to one another as image and mirror image (diastereomers). The present invention relates both to the antipodes and also to the racemic forms and to the mixtures of diastereomers. The racemic forms can be separated, as can the diastereomers, into the homogeneous stereoisomeric components in a known manner (compare, for example, E. L. Eliel, Stereochemistry of Carbon Compounds, McGraw Hill, 1962).

The compounds of the general formula (I) exhibit interesting biological effects. They have a wide and diverse spectrum of pharmacological activity. The following major effects may be mentioned in particular:

1. The compounds, on parenteral, oral and perlingual administration, bring about a marked dilatation of the coronary vessels. This effect on the coronary vessels is reinforced by a relieving effect on the heart resembling that of nitrites. They effect or change the cardiac metabolism in the direction of a saving of energy.
2. The excitability of the pace-setting and stimulus-induction system within the heart is decreased, so that a detectable anti-fibrillatory effect results at therapeutic doses.
3. The tone of the smooth muscle of the vessels is greatly decreased under the action of the compounds.

This vasospasmolytic effect can take place in the entire vascular system or can manifest itself, in a more or less isolated fashion, in restricted vascular zones (such as, for example, in the brain).

4. The compounds decrease the blood pressure of normotensive and hypertensive animals and can thus be used as antihypertensive agents.

5. The compounds have strong muscular-spasmolytic effects, which become evident on the smooth muscle of the stomach, intestinal tract, urogenital tract and the respiratory system.

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compound, should, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose; starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, or course, also contain in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc, can be co-used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.01 to 10 mg/kg, preferably about 0.01 to 5 mg/kg of body weight daily to achieve effective results, and, in the case of oral administration, the dosage is about 0.1 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus, it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

EXAMPLE 1

Dimethyl 4-(2-benzylthiophenyl)-1,4-dihydro-2,6-dimethylpyridine-3,5-dicarboxylate

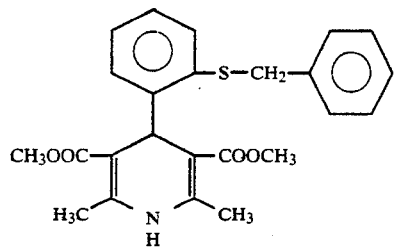

Process variant A

A solution of 100 mmols of methyl (2-benzylthio)benzylideneacetoacetate and 100 mmols of methyl β-aminocrotonate in 100 ml of methanol is heated to boiling for 24 hours.

The solvent is distilled off in vacuo and the residue is crystallized with a little ether.

Melting point: 84°-90° C.

Yield: 25%

EXAMPLE 2

Dimethyl 4-(2-benzyloxyphenyl)-1,4-dihydro-2,6-dimethylpyridine-3,5-dicarboxylate

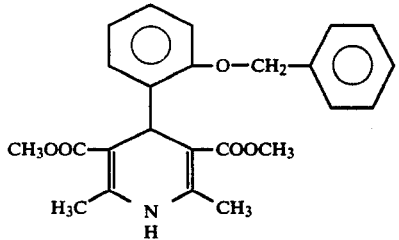

Process variant B

A solution of 100 mmols of methyl (2-benzyloxy)benzylideneacetoacetate, 100 mmols of methyl acetoacetate and 120 mmols of concentrated aqueous ammonia solution in 100 ml of ethanol was heated to boiling for 24 hours.

The solvent was distilled off in vacuo and the residue crystallized.

Melting point: 129°–135° C.

EXAMPLE 3

Diethyl 2-acetoxymethyl-4-(2-benzyloxyphenyl)-1,4-dihydro-6-methylpyridine-3,5-dicarboxylate

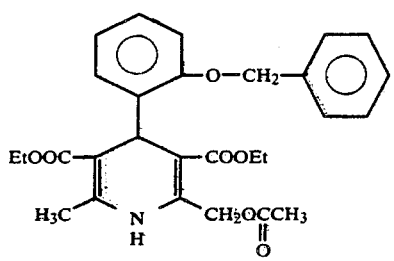

Process variant C 100 mmols of 2-benzyloxybenzaldehyde, 100 mmols of ethyl β-aminocrotonate and 100 mmols of ethyl 4-acetoxyacetoacetate in 100 ml of ethanol were heated to reflux for 12 hours.

The solvent was removed in vacuo and the residue was crystallized.

Melting point: 162°–165° C.

EXAMPLE 4

Dimethyl 1,4-dihydro-2,6-dimethyl-4-[(2-phenylthiomethyloxy)-phenyl]-3,5-dicarboxylate

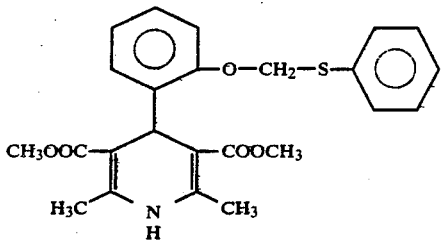

Process variant D 100 mmols of 2-(phenylthiomethyloxy)-phenylbenzaldehyde, 200 mmols of methyl acetoacetate and 120 mmols of concentrated aqueous ammonia solution in 100 ml of ethanol were boiled under reflux for 12 hours, the solvent was removed by distillation and the residue was crystallized.

Melting point: 159° C.

The following compounds were prepared in analogy to Examples 1-4:

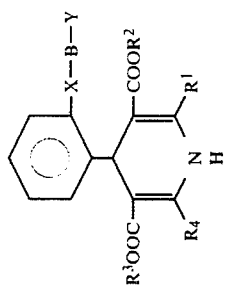

| Example | R$^3$ | R$^4$ | R$^1$ | R$^2$ | X—B | Y | melting point/°C. | Yield (preparation process) |
|---|---|---|---|---|---|---|---|---|
| 5 | —C$_2$H$_5$ | —CH$_2$OC(=O)—CH$_3$ | —CH$_2$OC(=O)—CH$_3$ | —C$_2$H$_5$ | —O—CH$_2$— | phenyl | 202-204 | 45% (D) |
| 6 | —C$_2$H$_5$ | —CH$_2$OC(=O)—CH$_3$ | —CH$_3$ | —CH$_3$ | —O—CH$_2$— | phenyl | 137 | 60% (C) |
| 7 | —CH$_3$ | —CH$_3$ | —CH$_3$ | —CH$_3$ | —S— | phenyl | 146 | 48% (C) |
| 8 | —CH$_3$ | —CH$_3$ | —CH$_3$ | —CH$_3$ | —S—CH$_2$— | 4-CH$_3$-phenyl | 145-146 | 20% (C) |
| 9 | —C$_2$H$_5$ | —CH$_3$ | —CH$_3$ | —C$_2$H$_5$ | —CH$_2$— | phenyl | 130-133 | 42% (C) |
| 10 | —C$_2$H$_5$ | —CH$_3$ | —CH$_3$ | —C$_2$H$_5$ | —S—CH$_2$— | 3,4-di-Cl-phenyl | 138 | 35% (D) |

-continued
The following compounds were prepared in analogy to Examples 1-4:
| | | | | | | |
|---|---|---|---|---|---|---|
| 11 | —C₂H₅ | —CH₃ | —CH₃ | —C₂H₅ | —S—CH₂ |  amorphous 40% (C) |
| 12 | —CH₂—CH₂CN | —CH₃ | —CH₃ | —CH₃ | —S—CH₂ |  128-130 40% (C) |
| 13 | —C₂H₅ | —CH₃ | —CH₃ | —CH₃ | —S—CH₂ |  54-57 25% (C) |
| 14 | —(CH₂)₂OCH₃ | —CH₃ | —CH₃ | —CH₃ | —S—CH₂ |  145-149 45% (C) |
| 15 | " | —CH₃ | —CH₃ | —C₂H₅ | —S—CH₂ |  114-116 40% (C) |
| 16 | —(CH₂)₂N(CH₃)₂ | —CH₃ | —CH₃ | —(CH₂)₂N(CH₃)₂ | —S—CH₂ |  95-104 55% (D) |
| 17 | —C₂H₅ | $-CH_2OC\overset{O}{\|}-CH_3$ | —CH₃ | —C₂H₅ | —O—CH₂ |  159-160 45% (C) |

-continued

The following compounds were prepared in analogy to Examples 1-4:

| No. | | | | | | |
|---|---|---|---|---|---|---|
| 18 | —(CH$_2$)$_2$—N(CH$_3$)$_2$ | —CH$_3$ | —CH$_3$ | —S—CH$_2$ | phenyl | 88-94 | 45% (C) |
| 19 | —(CH$_2$)$_2$CN | —CH$_3$ | —CH$_3$ | —S—CH$_2$ | 4-CH$_3$-phenyl | 163-165 | 44% (C) |
| 20 | —C$_2$H$_5$ | —CH$_2$—NH$_2$ | —CH$_3$ | —S—CH$_2$ | phenyl | 150 | 25% (C) |
| 21 | —CH$_3$ | —CH$_3$ | —CH$_3$ | —O—CH$_2$ | 4-Cl-phenyl | 210 | 43% (D) |
| 22 | —CH$_3$ | —CH$_3$ | —CH$_3$ | —O—CH$_2$ | 2-Cl-phenyl | 166 | 39% (D) |
| 23 | —CH$_3$ | —CH$_3$ | —CH$_3$ | —O—CH$_2$ | 2,6-(CH$_3$)$_2$-phenyl | 205 | 38% (D) |
| 24 | —CH$_3$ | —CH$_3$ | —CH$_3$ | —O—CH$_2$ | 3,4-Cl$_2$-phenyl | 143 | 44% (D) |

-continued

The following compounds were prepared in analogy to Examples 1–4:

| | | | | | | |
|---|---|---|---|---|---|---|
| 25 | —CH₃ | —CH₃ | —CH₃ | —O—CH₂ | ![Ph-CH₃] | 177 | 71% (D) |
| 26 | —CH₃ | —CH₃ | —CH₃ | —O—CH₂CH₂ | ![Ph] | 154 | 26% (D) |
| 27 | —CH₃ | —CH₃ | —CH₃ | —O—CH₂ | ![Ph] | 183 | 65% (D) |
| 28 | —CH₃ | —CH₃ | —CH₃ | —CH₂(CH=CH₂—CH₂)—H | ![Ph] | 158 | 32% (D) |
| 29 | —CH₃ | —CH₃ | —CH₃ | —OCH₂CH₂O— | | 170 | 22% (D) |
| 30 | —CH₃ | —CH₃ | —(CH₂)₂CN | —O—CH₂— | ![Ph-CO₂C₂H₅] | from 108 | 30% (C) |
| 31 | —CH₃ | —CH₃ | —(CH₂)₂CN | —O—CH₂— | ![Ph] | 165 | 40% (C) |
| 32 | —CH₃ | —CH₃ | —(CH₂)₂CN | —O—CH₂— | ![Ph-CH₃] | 189 | 44% (C) |
| 33 | —CH₃ | —CH₃ | —(CH₂)₂CN | —O—CH₂— | ![Ph-Cl] | 165 | 54% (C) |

(Note: Row 33 aromatic substituent is 2,3-dichlorophenyl shown with two Cl groups)

-continued

The following compounds were prepared in analogy to Examples 1-4:

| | | | | | | | |
|---|---|---|---|---|---|---|---|
| 41 | CH₃<br>−CH−CH₂−CH₃ | −CH₃ | −CH₃ | −(CH₂)₂CN | −O−CH₂− | 4-CH₃-C₆H₄ | 183-185 | 50% (C) |
| 42 | CH₃<br>−CH₂−CH<br>CH₃ | −CH₃ | −CH₃ | −(CH₂)₂CN | −O−CH₂− | 2-CF₃-C₆H₄ | 175-178 | 67% (C) |
| 43 | CH₃<br>−CH−CH₂−CH₃ | −CH₃ | −CH₃ | −(CH₂)₂CN | −O−CH₂− | 3-CF₃-C₆H₄ | 130-131 | 41% (C) |
| 44 | −CH₃ | −CH₃ | −CH₃ | −(CH₂)₂CN | −O−CH₂− | 2-NO₂-C₆H₄ | 178-183 | 70% (C) |
| 45 | −C₂H₅ | −CH₃ | −CH₃ | −(CH₂)₂CN | −O−CH₂− | 3-NO₂-C₆H₄ | 172-174 | 62% (C) |
| 46 | −CH₃ | −CH₃ | −CH₃ | −(CH₂)₂CN | −O−CH₂− | 4-F-C₆H₄ | 193-196 | 53% (C) |
| 47 | −C₂H₅ | −CH₃ | −CH₃ | −(CH₂)₂CN | −O−CH₂− | 4-F-C₆H₄ | 198-200 | 48% (C) |
| 48 | −CH₃ | −CH₃ | −CH₃ | −(CH₂)₂CN | −S−CH₂−CH₂−CH₂ | C₆H₅ | amorphous | 95% (C) |

-continued

The following compounds were prepared in analogy to Examples 1-4:

| # | R1 | R2 | R3 | Chain | Aryl | mp | Yield |
|---|---|---|---|---|---|---|---|
| 34 | —CH$_3$ | —CH$_3$ | —CH$_3$ | ─(CH$_2$)$_2$CN | —O—CH$_2$— | 2,6-dichlorophenyl | 192–194 | 69% (C) |
| 35 | —CH$_3$ | —CH$_3$ | —CH$_3$ | ─(CH$_2$)$_2$CN | —OCH$_2$CH$_2$— | phenyl | 163–164 | 54% (C) |
| 36 | —CH$_3$ | —CH$_3$ | —CH$_3$ | ─(CH$_2$)$_2$CN | —O—CH$_2$— | 3,4-dichlorophenyl | 191–192 | 46% (C) |
| 37 | —CH(CH$_3$)$_2$ | —CH$_3$ | —CH$_3$ | ─(CH$_2$)$_2$CN | —O—CH$_2$— | 4-methylphenyl | 199–200 | 59% (C) |
| 38 | —CH$_3$ | —CH$_3$ | —CH$_3$ | ─(CH$_2$)$_2$CN | —O—CH$_2$ | 3-CF$_3$-phenyl | 152–154 | 61% (C) |
| 39 | —CH$_3$ | —CH$_3$ | —CH$_3$ | ─(CH$_2$)$_2$CN | —S—CH$_2$— | 3-CF$_3$-phenyl | amorphous | 90% (C) |
| 40 | —CH$_2$—CH(CH$_3$)$_2$ | | | ─(CH$_2$)$_2$CN | —O—CH$_2$— | 4-methylphenyl | 177–178 | 60% (C) |

-continued

The following compounds were prepared in analogy to Examples 1–4:

| | | | | | | | |
|---|---|---|---|---|---|---|---|
| 49 | —CH$_3$ | —CH$_3$ | —CH$_3$ | ―(CH$_2$)$_2$CN | —O—CH$_2$— | 3,5-(CH$_3$)$_2$-C$_6$H$_3$ | 168–170 | 50% (C) |
| 50 | —(CH$_2$)$_3$—CH$_3$ | —CH$_3$ | —CH$_3$ | ―(CH$_2$)$_2$CN | —O—CH$_2$— | 3,5-(CH$_3$)$_2$-C$_6$H$_3$ | 160–161 | 42% (C) |
| 51 | —CH$_3$ | —CH$_3$ | —CH$_3$ | ―(CH$_2$)$_2$CN | —O—CH$_2$— | 3-CH$_3$-C$_6$H$_4$ | 150–152 | 49% (C) |
| 52 | —(CH$_2$)$_3$CH$_3$ | —CH$_3$ | —CH$_3$ | ―(CH$_2$)$_2$CN | —O—CH$_2$— | 3-CH$_3$-C$_6$H$_4$ | 173–176 | 44% (C) |
| 53 | —CH$_3$ | —CH$_3$ | —CH$_3$ | ―(CH$_2$)$_2$CN | —O—CH$_2$— | 3-F-C$_6$H$_4$ | 147–149 | 43% (C) |
| 54 | —(CH$_2$)$_3$CH$_3$ | —CH$_3$ | —CH$_3$ | —(CH$_2$)$_2$CN | —O—CH$_2$— | 3-F-C$_6$H$_4$ | 182–185 | 53% (C) |

-continued

The following compounds were prepared in analogy to Examples 1-4:

| | | | | | | |
|---|---|---|---|---|---|---|
| 55 | —CH₃ | —CH₃ | —CH₃ | —(CH₂)₂CN | —O—CH₂— | 3-OCH₃-phenyl | 138–142 | 56% (C) |
| 56 | —(CH₂)₃—CH₃ | —CH₃ | —CH₃ | —(CH₂)₂CN | —O—CH₂— | 3-OCH₃-phenyl | 128–131 | 43% (C) |
| 57 | —CH₃ | —CH₃ | —CH₃ | —(CH₂)₂CN | —O—CH₂— | pyridyl | amorphous$^+$ RF-value = 0.14 | 88% (C) |
| 58 | —(CH₂)₃CH₃ | —CH₃ | —CH₃ | —(CH₂)₂CN | —O—CH₂— | pyridyl | amorphous$^+$ RF-value = 0.16 | 95% (C) |
| 59 | —CH₃ | —CH₃ | —CH₃ | —(CH₂)₂CN | —OCH₂S— | phenyl | amorphous$^+$ RF-value = 0.62 | 93% (C) |
| 60 | —CH₃ | —CH₃ | —CH₃ | —CH₃ | —S—CH₂— | cyclohexyl | 142–156 | 30% (D) |
| 61 | —C₂H₅ | —CH₃ | —CH₃ | —C₂H₅ | —S—CH₂— | cyclohexyl | 209–211 | 55% (D) |
| 62 | —(CH₂)₂OCH₃ | —CH₃ | —CH₃ | —(CH₂)₂OCH₃ | —S—CH₂— | cyclohexyl | 84–87 | 25% (D) |

-continued

The following compounds were prepared in analogy to Examples 1-4:

| No. | | | | | Ar | mp | yield |
|---|---|---|---|---|---|---|---|
| 63 | —CH₃ | —CH₃ | —CH₃ | —OSO₂— | 4-CH₃-C₆H₄ | amorphous | 40% (D) |
| 64 | —C₂H₅ | —CH₃ | —C₂H₅ | —OSO₂— | 4-CH₃-C₆H₄ | 145 | 38% (D) |
| 65 | —CH₃ | —CH₃ | —CH₃ | —OCH₂— | 2-thienyl | 162 | 18% (D) |
| 66 | —CH₃ | —CH₃ | —CH₃ | —OCH₂— | C₆F₅ | 160 | 20% (D) |
| 67 | —CH₃ | —CH₃ | —CH₃ | —OCH₂— | 4-CH₃-C₆H₄ | 160 | 20% (D) |
| 68 | —CH₃ | —CH₃ | —CH₃ | —OCH₂— | 3,5-(CH₃)₂-C₆H₃ | 188 | 35% (D) |
| 69 | —CH₃ | —CH₃ | —CH₃ | —OCH₂— | 3-F-C₆H₄ | 132 | 42% (D) |

-continued

The following compounds were prepared in analogy to Examples 1-4:

| 70 | —CH₃ | —CH₃ | —CH₃ | —CH₃ | —OCH₂— | [naphthyl-CH₃] | 153 | 20% (D) |
| 71 | —CH₃ | —CH₃ | —CH₃ | —CH₃ | —OSO₂— | [thienyl] | 132 | 20% (D) |

Structure:

R⁶—[phenyl with X—B—Y substituent]—[dihydropyridine ring with COOR², CH₃, R³, H₃C, NH]

| Example | R³ | R² | X—B | Y | R⁶ | melting point/°C | Yield (Preparation process) |
|---|---|---|---|---|---|---|---|
| 72 | —CH₃ | —CH₃ | —OCH₂— | [3-methoxyphenyl] | 3-OCH₃ | 189 | 31% (D) |
| 73 | —C₂H₅ | —C₂H₅ | —S—CH₂— | [4-methylphenyl] | 5-NO₂ | 175–178 | 45% (D) |

†Ready-coated TLC plates, silica gel 60 F₂₅₄ (Merck), mobile phase, CHCl₃/ethyl acetate = 3:1

It will be appreciated that the instant specification and examples are set forth by way of illustration and not limitation, and that various modifications and changes may be made without departing from the spirit and scope of the present invention.

We claim:

1. A 1,4-dihydropyridine of the formula

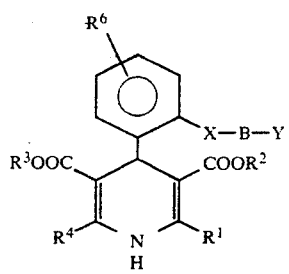

in which

R¹ and R⁴ each independently is hydrogen or an alkyl radical having up to 6 carbon atoms which optionally contains 1 or 2 chain members independently selected from the group consisting of O, CO and NH, R² and R³ each independently is an alkyl or alkenyl radical having up to 6 carbon atoms, which is optionally substituted by halogen, hydroxyl, cyano, amino, monoalkylamino, dialkylamino or alkyl-benzylamino, the alkyl radicals mentioned each containing 1 to 4 carbon atoms, R⁶ is 1 or 2 substituents independently selected from the group consisting of hydrogen, chloro, nitro and alkyl or alkoxy each having 1 to 4 carbon atoms, X is a bridging member selected from the group consisting of O and S, B is an alkylene group having 1 to 4 carbon atoms or a direct bond (excepting X—B—Y=—O—O—), and y is cyclohexyl, being either directly bonded to B or bonded to B via a hetero member selected from the group consisting of O, S, SO, SO₂, NH and N-alkyl having 1 to 4 carbon atoms, and optionally containing substituents independently selected from the group consisting of nitro, halogen, trifluoromethyl, cyano, hydroxyl, phenyl, ethoxycarbonyl and alkyl or alkoxy each having 1 to 4 carbon atoms, or a pharmaceutically acceptable addition salt thereof.

2. A compound or salt according to claim 1, in which R² and R³ each independently is an alkyl radical having up to 6 carbon atoms, which is optionally substituted by halogen, hydroxyl, cyano, monoalkylamino, dialkylamino or alkyl-benzylamino, the alkyl radicals mentioned each containing 1 to 4 carbon atoms.

3. A compound according to claim 1, wherein such compound is dimethyl 4-(2-benzylthiophenyl)-1,4-dihydro-2,6-dimethylpyridine-3,5-dicarboxylate of the formula

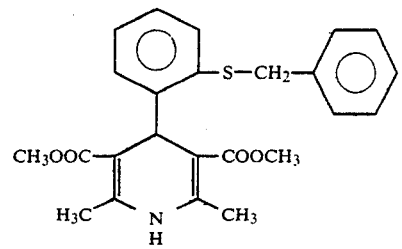

or a pharmaceutically acceptable addition salt thereof.

4. A compound according to claim 1, wherein such compound is dimethyl 4-(2-benzyloxyphenyl)-1,4-dihydro-2,6-dimethylpyridine-3,5-dicarboxylate of the formula

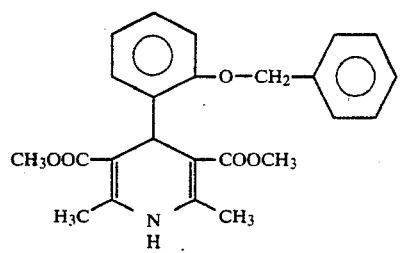

or a pharmaceutically acceptable addition salt thereof.

5. A compound according to claim 1, wherein such compound is dimethyl 2-acetoxymethyl-4-(2-benzyloxyphenyl)-1,4-dihydro-6-methylpyridine-3,5-dicarboxylate of the formula

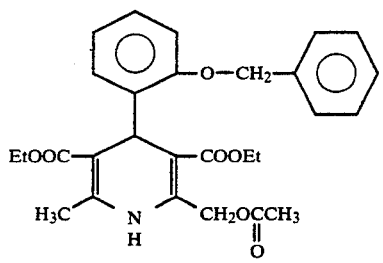

or a pharmaceutically acceptable addition salt thereof.

6. A compound according to claim 1, wherein such compound is dimethyl 1,4-dihydro-2,6-dimethyl-4-[(2-phenylthiomethyloxy) phenyl]-3,5-dicarboxylate of the formula

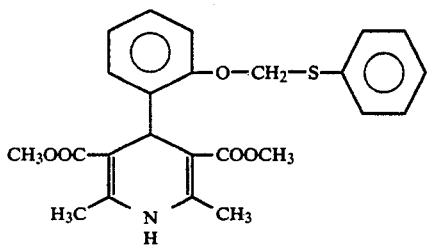

or a pharmaceutically acceptable addition salt thereof.

7. A compound according to claim 1, wherein such compound is diethyl 4-(2-(3,4-dichlorobenzyl)-thiophenyl)-1,4-dihydro-2,6-dimethyl-pyridine-3,5-dicarboxylate of the formula

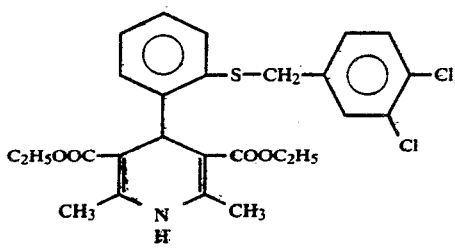

or a pharmaceutically acceptable addition salt thereof.

8. A compound according to claim 1, wherein such compound is ethyl cyanoethyl 4-(2-p-tolylmethylthiophenyl)-1,4-dihydro-2,6-dimethyl-pyridine-3,5-dicarboxylate of the formula

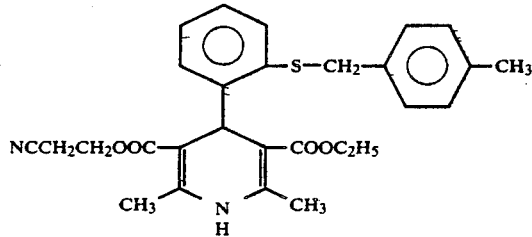

or a pharmaceutically acceptable addition salt thereof.

9. A compound according to claim 1, wherein such compound is diethyl 4-(2-cyclohexylmethylthiophenyl)-1,4-dihydro-2,6-dimethyl-pyridine-3,5-carboxylate of the formula

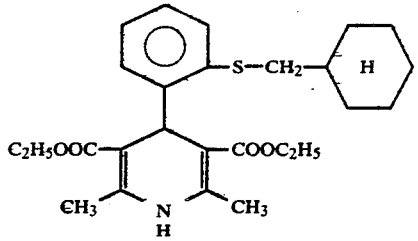

or a pharmaceutically acceptable addition salt thereof.

10. A hypotensive composition comprising a hypotensive amount of a compound or salt according to claim 1 in admixture with a pharmaceutically acceptable diluent.

11. A composition according to claim 10, in the form of tablets, pills, dragees, capsules, ampules or suppositories.

12. A method of lowering blood pressure in human and non-human animals which comprises administering to such animal a hypotensive amount of a compound or salt according to claim 1.

13. A method according to claim 12, wherein such compound is
dimethyl 4-(2-benzylthiophenyl)-1,4-dihydro-2,6-dimethylpyridine-3,5-dicarboxylate,
dimethyl 4-(2-benzyloxyphenyl)-1,4-dihydro-2,6-dimethylpyridine-3,5-dicarboxylate,
dimethyl 2-acetoxymethyl-4-(2-benzyloxyphenyl)-1,4-dihydro-6-methylpyridine-3,5-dicarboxylate,
dimethyl 1,4-dihydro-2,6-dimethyl-4-[(2-phenylthiomethyloxy) phenyl]-3,5-dicarboxylate,
diethyl 4-(2-(3,4-dichlorobenzyl)-thiophenyl)-1,4-dihydro-2,6-dimethyl-pyridine-3,5-dicarboxylate,
ethyl cyanoethyl 4-(2-p-tolylmethylthiophenyl)-1,4-dihydro-2,6-dimethyl-pyridine-3,5-dicarboxylate,
diethyl 4-(2-cyclohexylmethylthiophenyl)-1,4-dihydro-2,6-dimethyl-pyridine-3,5-carboxylate
or a pharmaceutically acceptable addition salt thereof.

* * * * *